(12) United States Patent
Schröder et al.

(10) Patent No.: US 7,402,576 B2
(45) Date of Patent: *Jul. 22, 2008

(54) PHOSPHINIC ACID ANALOGS OF GLUTAMATE

(75) Inventors: Fridtjof Schröder, Hettlingen (CH); Andreas Natsch, Uetikon (CH)

(73) Assignee: Givaudan SA, Vernier (CH)

( * ) Notice: Subject to any disclaimer, the term of this patent is extended or adjusted under 35 U.S.C. 154(b) by 344 days.

This patent is subject to a terminal disclaimer.

(21) Appl. No.: 10/534,528

(22) PCT Filed: Nov. 14, 2003

(86) PCT No.: PCT/CH03/00750

§ 371 (c)(1), (2), (4) Date: May 11, 2005

(87) PCT Pub. No.: WO2004/043971

PCT Pub. Date: May 27, 2004

(65) Prior Publication Data

US 2006/0052616 A1    Mar. 9, 2006

(30) Foreign Application Priority Data

Nov. 14, 2002    (GB) ................... 0226550.2

(51) Int. Cl.
*A61K 31/66* (2006.01)
*C07F 9/22* (2006.01)
(52) U.S. Cl. ........................................ 514/114; 562/11
(58) Field of Classification Search ............... 562/11; 514/114

See application file for complete search history.

(56) References Cited

FOREIGN PATENT DOCUMENTS

EP        0 265 412 A      4/1988
WO     WO 02/092024 A2   11/2002

OTHER PUBLICATIONS

Search Report dated Apr. 15, 2003 from The Patent Office in Great Britain for Application GB 0226550.2.

*Primary Examiner*—Rei-Tsang Shiao

(57) ABSTRACT

Inhibitors of axillary malodour having the formula

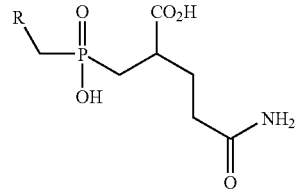

wherein R has the same meaning as given in the specification.

5 Claims, No Drawings

SEQUENCE LISTING

<160> NUMBER OF SEQ ID NOS: 2

<210> SEQ ID NO 1
<211> LENGTH: 399
<212> TYPE: PRT
<213> ORGANISM: Corynebacterium striatum

<400> SEQUENCE: 1

Ala Gln Glu Asn Leu Gln Lys Ile Val Asp Ser Leu Glu Ser Ser Arg
 1               5                  10                  15

```
Ala Glu Arg Glu Glu Leu Tyr Lys Trp Phe His Gln His Pro Glu Met
            20                  25                  30

Ser Met Gln Glu His Glu Thr Ser Lys Arg Ile Ala Glu Glu Leu Glu
            35                  40                  45

Lys Leu Gly Leu Glu Pro Gln Asn Ile Gly Val Thr Gly Gln Val Ala
            50                  55                  60

Val Ile Lys Asn Gly Glu Gly Pro Ser Val Ala Phe Arg Ala Asp Phe
65                  70                  75                  80

Asp Ala Leu Pro Ile Thr Glu Asn Thr Gly Leu Asp Tyr Ser Ala Asp
                    85                  90                  95

Pro Glu Leu Gly Met Met His Ala Cys Gly His Asp Leu His Thr Thr
                100                 105                 110

Ala Leu Leu Gly Ala Val Arg Ala Leu Val Glu Asn Lys Asp Leu Trp
            115                 120                 125

Ser Gly Thr Phe Ile Ala Val His Gln Pro Gly Glu Glu Gly Gly Gly
            130                 135                 140

Gly Ala Arg His Met Val Asp Asp Gly Leu Ala Glu Lys Ile Ala Ala
145                 150                 155                 160

Pro Asp Val Cys Phe Ala Gln His Val Phe Asn Glu Asp Pro Ala Phe
                165                 170                 175

Gly Tyr Val Phe Thr Pro Gly Arg Phe Leu Thr Ala Ala Ser Asn Trp
                180                 185                 190

Arg Ile His Ile His Gly Glu Gly Gly His Gly Ser Arg Pro His Leu
                195                 200                 205

Thr Lys Asp Pro Ile Val Val Ala Ser Ile Ile Thr Lys Leu Gln
            210                 215                 220

Thr Ile Val Ser Arg Glu Val Asp Pro Asn Glu Val Ala Val Val Thr
225                 230                 235                 240

Val Gly Ser Ile Glu Gly Gly Lys Ser Thr Asn Ser Ile Pro Tyr Thr
                245                 250                 255

Val Thr Leu Gly Val Asn Thr Arg Ala Ser Asn Asp Glu Leu Ser Glu
            260                 265                 270

Tyr Val Gln Asn Ala Ile Lys Arg Ile Val Ile Ala Glu Cys Gln Ala
            275                 280                 285

Ala Gly Ile Glu Gln Glu Pro Glu Phe Glu Tyr Leu Asp Ser Val Pro
            290                 295                 300

Ala Val Ile Asn Asp Glu Asp Leu Thr Glu Gln Leu Met Ala Gln Phe
305                 310                 315                 320

Arg Glu Phe Phe Gly Glu Asp Gln Ala Val Glu Ile Pro Pro Leu Ser
                325                 330                 335

Gly Ser Glu Asp Tyr Pro Phe Ile Pro Asn Ala Trp Gly Val Pro Ser
                340                 345                 350

Val Met Trp Gly Trp Ser Gly Phe Ala Ala Gly Ser Asp Ala Pro Gly
            355                 360                 365

Asn His Thr Asp Lys Phe Ala Pro Glu Leu Pro Asp Ala Leu Glu Arg
            370                 375                 380

Gly Thr Gln Ala Ile Leu Val Ala Ala Pro Trp Leu Met Lys
385                 390                 395
```

<210> SEQ ID NO 2
<211> LENGTH: 1212
<212> TYPE: DNA
<213> ORGANISM: Corynebacterium striatum -continued

```
<400> SEQUENCE: 2
aatcgggtca tggcacagga aaatttgcaa aagattgtag atagtctcga gtcctcccgc    60
gcggaacgcg aagaactgta caagtggttc caccagcacc cggaaatgtc gatgcaggag   120
cacgaaacct ccaagcgcat cgcagaagag ctagagaagc tcggccttga gccgcagaac   180
atcggcgtga ccgggcaggt cgcggtaatc aagaacggtg aaggcccgag cgtggcattt   240
cgtgcggact ttgatgcctt gccgatcacc gagaacaccg ggctggatta ctcggcggat   300
cccgagctgg gcatgatgca cgcctgcggc cacgatttgc acaccactgc cctactcggc   360
gcggtgcgcg cgctggtgga gaacaaggac ctgtggtccg gcaccttcat cgcagtccac   420
caacccggtg aggaaggcgg cggcggggcc cgccacatgg tggacgacgg cctcgcggag   480
aagatcgcgg cgccggatgt gtgtttcgcc cagcacgtgt tcaacgaaga ccccgccttt   540
ggctacgtgt tcaccccccgg ccggtttcta acggcggcgt cgaactggag aatccacatc   600
cacggcgagg gcggacacgg ttcccgtccg cacctgacca aggacccgat tgtggtggcg   660
gcctcgatca ttaccaagct gcagacgatt gtctcccgcg aagtcgatcc gaatgaggtc   720
gcagtggtca ccgtcggctc catcgagggc ggcaagtcca ccaactcgat cccgtacacc   780
gtcaccctcg gcgtgaacac ccgagcctcc aacgatgagc tctccgagta cgtccagaac   840
gccatcaagc gcatcgtcat cgcggagtgc caggctgcag gcatcgaaca ggagccggaa   900
ttcgagtacc tggactcagt cccggccgtg atcaacgacg aggatctcac cgaacagctc   960
atggcgcagt tccgggagtt cttcggcgag gaccaggcgg tagagattcc gcccctgtcc  1020
ggcagcgagg actaccccctt cattccgaac gcctggggcg tgccgagtgt gatgtgggga  1080
tggtccggct tcgccgcagg ttctgacgca ccgggcaatc acaccgacaa gttcgccccc  1140
gagcttccag atgccctcga acgcggcacc caggccattc tggtggccgc cgcgccctgg  1200
ttgatgaagt ga                                                       1212
```

PHOSPHINIC ACID ANALOGS OF GLUTAMATE

This application is a 371 of PCT/CH03/00750 filed of Nov. 14, 2003.

This invention is concerned with compounds useful for the prevention or suppression of human malodour, in particular human axillary malodour.

It is known that fresh sweat is odourless and that odour is only formed upon contact of sweat with skin bacteria (for example bacteria of the genera of *Staphylococcus* and *Corynebacteria*) and it is believed that odourless molecules present in sweat are degraded by bacteria colonising the axilla. It is generally accepted (Labows et. al., Cosmet. Sci Technol. Ser. (1999), 20:59-82) that highly unpleasant malodour is released from fresh sweat mainly by the *Corynebacteria* genus of bacteria. The principal constituents thought to be responsible for malodour include volatile steroids, volatile sulphur compounds and short-chain, branched fatty acids.

It has been suggested to treat malodour by eradicating the bacteria responsible for causing the odour. Indeed, commercially available cosmetic deodorants often contain antibacterial compounds that generally inhibit the growth of skin microflora. Antibacterial compounds currently used in deodorant products include, for example Triclosan (2,4,4'-trichloro-2'hydroxy-diphenyl-ether). However, a draw-back to the use of antibacterials is the potential for disturbing the equilibrium of the skin's natural microflora.

Fatty acids, in particular short chain, branched fatty acids are known to play a role in axillary malodour, and are particularly foul smelling components of stale sweat. In co-pending application PCT/CH02/00262 the applicant has disclosed an enzyme that mediates in a process of transforming odourless compounds found in sweat into these malodorous fatty acids. In this co-pending application there is also disclosed a broad class of compounds having activity as inhibitors of the enzyme.

Nevertheless there remains the need to find further compounds displaying good inhibitory properties with respect to the above mentioned enzyme.

Accordingly, the invention provided in a first aspect a compound of formula (I)

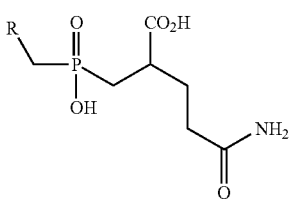

wherein R is a substituted alkyl, benzyl or allyl residue selected from the group consisting of
a) nonyl;
b) 3,3,3-trifluoro-propyl;
c) 2-methyl-4-phenyl-butyl;
d) 4-trifluoromethyl-phenyl;
e) pentafluorophenyl;
f) 4-fluoro-phenyl;
g) naphthalene-2-yl;
h) biphenyl-2-yl;
i) 5,5,7,8,8-pentamethyl-5,6,7,8-tetrahydro-naphthalene-2-yl;
k) 5,5,8,8-tetramethyl-5,6,7,8-tetrahydro-naphthalen-2-yl;
l) 1,1,3,3-tetramethyl-indan-5-yl;
m) styryl;
n) 2,6-dimethyl-heptyl;
o) 2-(4-tert-Butyl-phenyl)-1-methyl-vinyl;
p) 2-(4-Isopropyl-phenyl)-1-methyl-vinyl;
q) 1-(1,7,7-Trimethyl-bicyclo[2.2.1]hept-2-yl)-ethyl;
r) 2-(4-Isobutyl-phenyl)-1-methyl-vinyl;
s) 2-(2-isopropyl-phenyl)-1-methyl-ethenyl;
t) 2-phenyl-ethyl;
u) cyclohexyl-methyl;
v) 2,2-dimethyl-propyl;
w) 2-(pentafluorophenyl)-ethyl;
x) 3-phenyl-propyl;
y) heptyl;
z) 4-isopropyl-cyclohex-1-enyl;
za) decyl;
zb) hexyl;
zc) trans-4-isopropyl-cyclohexyl;
zd) 5-ethyl-2-methyl-heptyl;
ze) 2,6,10-trimethyl-undecyl;
zf) 1-methyl-3-(2,2,3-trimethyl-cyclopentyl)-propyl; and
zg) octyl.

Compounds of the formula (I) contain chiral atoms and as such they can exist as isomeric mixtures or they may exist as pure stereoisomers. Most preferred are compounds have an S-configuration on the carbon atom in the position alpha to the carboxyl group.

As stated hereinabove, compounds of the present invention may interact with an enzyme thereby to reduce the enzyme's ability to cleave compounds in sweat leading to release of malodorous acids from odourless fresh sweat. That enzyme, described in the aforementioned co-pending application, was isolated from the bacteria of the genus *Corynebacteria* that can be found colonising the axilla, in particular certain *Corynebacteria* sp., more particularly *Corynebacterium striatum* Ax 20 which has been submitted on the 26, Apr. 2001 to the International Depository Authority DSMZ-Deutsche Sammlung von Mikrooganismen und Zellkulturen GmbH, D-38124 Braunschweig. The Accession Number provided by the International Depository Authority is DSM 14267. The enzyme was found to occur intracellularly and can be released from the cells by mechanical disruption of the cell envelope. Thus, it may be isolated from cellular extracts obtained from wild-type bacterial strains, especially from strains of *Corynebacteria* isolated from the human axilla, in particular *Corynebacterium striatum* Ax 20. In the alternative, it may be produced by recombinant means which are well known to persons skilled in the art.

The amino acid sequence of this enzyme is set forth in SEQ ID No. 1 and a nucleic acid sequence encoding for this enzyme is set forth in SEQ ID No. 2, both of which sequences are shown below.

Compounds of the present invention display inhibition of the enzyme at concentrations of about 1 to 500, nanomolar more particularly from 5 nanomolar 500 nanomolar concentration in vitro, e.g. from 9 to 150 nanomolar. Furthermore, having regard to the lipophilicity of the residue R, the compounds are adapted to penetrate the cell walls of the enzyme-producing bacteria, as such, they are efficaceous in vivo.

Indeed, the nature of the residue R appears to influence the ability of compounds to penetrate the cellular walls of different bacteria colonising the axilla and which are implicated in malodour production. For example, other strains of *Corynebacteria*, for example *Corynebacterium bovis* and *Corynebacterium jeikeium*, or bacteria of the genus *Staphylococci* found in the microflora of the axilla also produce related enzymes that themselves mediate in biochemical reactions wherein L-glutamine derivatives are cleaved at $N_\alpha$. The compounds of the present invention may interfere in cellular processes of a wide variety of bacterial strains thereby resulting in the suppression or prevention of malodour from these sources.

The in vitro activity of the compounds as inhibitors may be measured in terms of either their $IC_{50}$ values or their Ki values, both of which measures are well known to the person skilled in the art. As is well known, the $IC_{50}$ value provides the concentration of an inhibitor needed to reduce enzyme velocity by half at a given substrate concentration. This value is dependent on the affinity of the substrate for the enzyme which is reflected in the value $K_m$ of the substrate. In this way, the Ki value may be determined for a given substrate and a given substrate concentration by measuring $IC_{50}$ and then calculating according to the following formula $$K_i = \frac{IC_{50}}{1 + \frac{[Substrate]}{K_m}}$$

The uptake of the compounds in bacterial cells and the inhibition of the enzyme contained therein may be measured using an assay based on stationary-phase living cells. Thus, cells may be incubated along with inhibitory compound or compounds, and the substrate (i.e. the material found in sweat, which when cleaved by the enzyme forms the malodorous acids), and the release of acids may be measured at various inhibitor concentrations. By comparing $IC_{50}$ values obtained with the living cells with the $IC_{50}$ values obtained with the isolated enzyme, the ease of penetration of the compounds into the bacterial cells can be assessed.

Compounds of the present invention may be added to any cosmetic and personal care products such as sticks, roll-ons, pump-sprays, aerosols, deodorant soaps, powders, solutions, gels, creams, sticks, balms and lotions to enhance the deodorising effect of these products. Preferably, a compound of the present invention may be employed in said products in amounts of about 0.01 to 0.5% by weight.

The above-mentioned products, in addition to the inhibitors, may comprise anti-bacterial agents known in the art, e.g. Triclosan. The products may also comprise dermatologically acceptable ingredients such as are commonly used in these types of product. Examples of such additional ingredients include fragrances, colorants, opacifiers, buffers, antioxidants, vitamins, emulsifiers, UV absorbers, silicones and the like. As is also well known, all products can be buffered to the desired pH.

In addition to the inhibitor, a deodorant cologne may comprise ethanol and fragrance. Fragrance may be present from 1 to 10% and the ethanol can be present to make up the mass to 100%.

Additional ingredients in a typical ethanol-free deodorant stick may include polyols, such as propylene glycol; derivatives thereof, such as propylene-glycol-3-myristyl ether (Witconol APM); water; a surfactant such as sodium stearate; and fragrance. The polyol may be present in an amount of 30 to 40%; the derivatives of the polyol likewise may be present at about 30 to 40%; water may be present to about 10 to 20%; the surfactant may be present to 5 to 10%; and the fragrance may be present in an amount up to 10%.

A typical antiperspirant stick might contain as additional ingredients such as Ethylene Glycol Monostearate (e.g. from 5 to 10%); Shea butter (e.g. from 3 to 5%); Neobee 1053 (PVO International) (e.g. from about 12 to 15%); Generol 122 (Henkel) (e.g. from about 3 to 7%); Dimethicone (DC 345) (e.g. from 30 to 40%); aluminium sesquichlorohydrate (e.g. from about 15 to 20%); and a fragrance, e.g. from 1 to 10%.

An antiperspirant aerosol may contain ethanol, e.g. from about 10 to 15%; zirconium aluminium tetrachlorohydrate, e.g. from about 3 to 5%; Bentone 38, e.g. from about 1 to 2%; fragrance in an amount aforementioned; and a hydrocarbon propellant, e.g. S-31, up to 100% based on the total aerosol composition.

An antiperspirant pump composition may contain aluminium sesquichlorohydrate, e.g. from 15 to 25%; water, e.g. from 50 to 60%; Triton X-102 (Union carbide), e.g. from 1 to 3%; dimethyl Isosorbide (ICI), e.g. from 15 to 25%; and a fragrance in an amount as aforementioned.

All percentages mentioned above are in wt %.

Accordingly, the present invention relates to the use of the compounds of formula (I) and/or compositions containing same for the elimination or suppression of malodour. The invention also relates to compositions comprising an odour-suppressing quantity of an inhibitor compound, which acts as an inhibitor of the enzyme, and dermatologically acceptable vehicles that are generally well known in the art of cosmetic and personal care products.

The invention also provides in another of its aspects, a method of suppressing axillary malodour comprising the step of providing a composition for application to the skin of a person in need of treatment, said composition containing an inhibitor compound and dermatologically acceptable vehicle therefor, said compound being selected from one or more compounds of formula (I) described above.

A compound of formula (I) may be prepared according to synthetic protocols as set out in detail below with reference to Scheme 1, Scheme 2 and the Examples

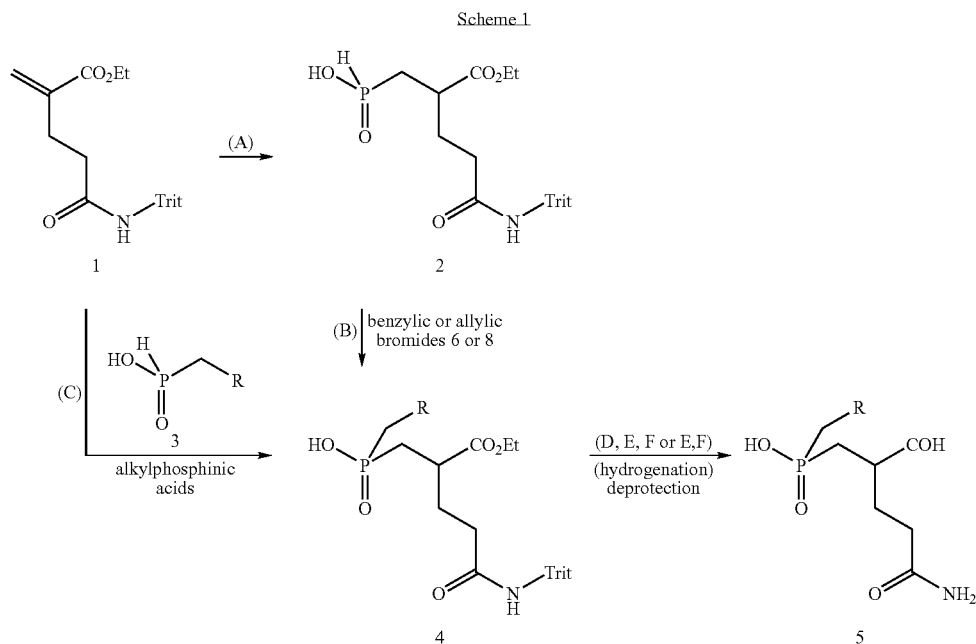

A) 5 equivalents (eq.) HP(OTMS)₂ for 2 h at 130° C.

B) 1 eq benzylic or allylic bromide (6 or 8), 3 eq BSA, at 25° C. The product (4) is obtained in quantitative yield.

C) 1 eq alkylphosphinic acid (3), 5 eq HMDS for 3 h at 130° C., then 1 eq acrylate (1) for 4 h at 130° C., then EtOH at 70° C. The product (4) is obtained in quantitative yield.

D) 10-20 weight-% Pt/C, 1 atm H₂, AcOEt/EtOH 2:1, 25° C. Or Raney-Ni, EtOH, 25° C., 1 atm H₂.

E) 1N LiOH/EtOH for 1 day at 25° C. to give the product in quantitative yield.

F) 2.2 eq (iPr)₃SiH in TFA at 25° C. for 3 h to provide compounds of the present invention.

The acrylate starting material (1) may be formed according to a method described in co-pending application PCT/CH02/00262.

The alkyl, benzyl or allyl halides (7,6,8) are either commercially available or may be formed from commonly available starting materials according to synthetic protocols known per se and set out in Scheme 2 below.

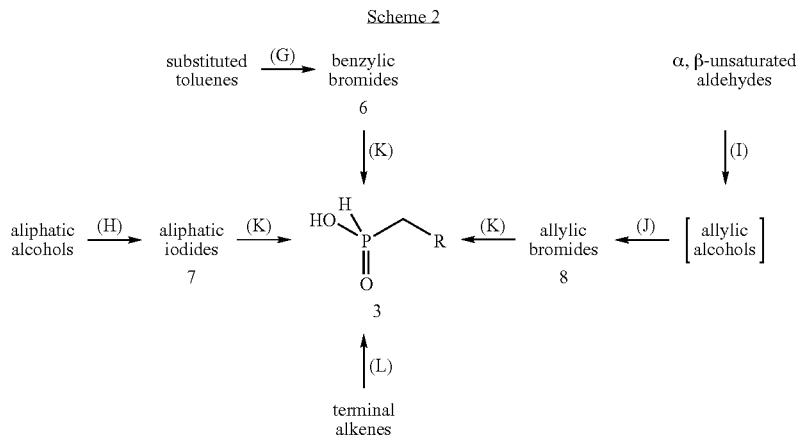

G) 1 eq Br₂ at 170° C. for 4 h.

H) 2 eq Pyridine, 1.2 eq PPh₃, 1.2 eq Iodine at 0° C. for 2 h.

I) 0.35 eq NaBH₄, MeOH for 2 h at 0° C., to provide the allylic alcohols in quantitative yield.

J) Et₂O, 0.4 eq PBr₃ for 5 h at 0° C. to provide the allylic bromides in quantitative yields.

K) 3-5 eq HP(OTMS)₂ in CH₂Cl₂, for 16 h.

L) 2 eq NaH₂PO₂(H₂O), 1 eq BEt₃, MeOH for 6 h at 25° C.

There now follows a series of Examples that serve to illustrate the invention.

EXAMPLES

The following compounds are formed according to the following syntheses:

5a 4-Carbamoyl-2-(decyl-hydroxy-phosphinoylmethyl)-butyric acid
5b 4-Carbamoyl-2-[hydroxy-(4,4,4-trifluoro-butyl)-phosphinoylmethyl]-butyric acid
5c 4-Carbamoyl-2-[hydroxy-(3-methyl-5-phenyl-pentyl)-phosphinoylmethyl]-butyric acid
5d 4-Carbamoyl-2-[hydroxy-(4-trifluoromethyl-benzyl)-phosphinoylmethyl]-butyric acid
5e 4-Carbamoyl-2-(hydroxy-pentafluorophenylmethyl-phosphinoylmethyl)-butyric acid
5f 4-Carbamoyl-2-[(4-fluoro-benzyl)-hydroxy-phosphinoylmethyl]-butyric acid
5g 4-Carbamoyl-2-(hydroxy-naphthalen-2-ylmethyl-phosphinoylmethyl)-butyric acid
5h 2-(Biphenyl-2-ylmethyl-hydroxy-phosphinoylmethyl)-4-carbamoyl-butyric acid
5i 4-Carbamoyl-2-[hydroxy-(5,5,7,8,8-pentamethyl-5,6,7,8-tetrahydro-naphthalen-2-ylmethyl)-phosphinoylmethyl]-butyric acid
5k 4-Carbamoyl-2-[hydroxy-(5,5,8,8-tetramethyl-5,6,7,8-tetrahydro-naphthalen-2-ylmethyl)-phosphinoylmethyl]-butyric acid
5l 4-Carbamoyl-2-[hydroxy-(1,1,3,3-tetramethyl-indan-5-ylmethyl)-phosphinoylmethyl]-butyric acid
5m E-4-Carbamoyl-2-[hydroxy-(3-phenyl-allyl)-phosphinoylmethyl]-butyric acid
5n 4-Carbamoyl-2-[(3,7-dimethyl-octyl)-hydroxy-phosphinoylmethyl]-butyric acid
5o E-2-{[3-(4-tert-Butyl-phenyl)-2-methyl-allyl]-hydroxy-phosphinoylmethyl}-4-carbamoyl-butyric acid
5p E-4-Carbamoyl-2-{hydroxy-[3-(4-isopropyl-phenyl)-2-methyl-allyl]-phosphinoylmethyl}-butyric acid
5q 4-Carbamoyl-2-{hydroxy-[2-(1,7,7-trimethyl-bicyclo[2.2.1]hept-2-yl)-propyl]-phosphinoylmethyl}-butyric acid
5r E-4-Carbamoyl-2-{hydroxy-[3-(4-isobutyl-phenyl)-2-methyl-allyl]-phosphinoylmethyl}-butyric acid
5s E-4-Carbamoyl-2-{hydroxy-[3-(2-isopropyl-phenyl)-2-methyl-allyl]-phosphinoylmethyl}-butyric acid
5t 4-Carbamoyl-2-[hydroxy-(3-phenyl-propyl)-phosphinoylmethyl]-butyric acid
5u 4-Carbamoyl-2-[(2-cyclohexyl-ethyl)-hydroxy-phosphinoylmethyl]-butyric acid
5v 4-Carbamoyl-2-[(3,3-dimethyl-butyl)-hydroxy-phosphinoylmethyl]-butyric acid
5w 4-Carbamoyl-2-[hydroxy-(2-pentafluorophenyl-ethyl)-phosphinoylmethyl]-butyric acid
5x 4-Carbamoyl-2-[hydroxy-(4-phenyl-butyl)-phosphinoylmethyl]-butyric acid
5y 4-Carbamoyl-2-(hydroxy-octyl-phosphinoylmethyl)-butyric acid
5z 4-Carbamoyl-2-[hydroxy-(4-isopropyl-cyclohex-1-enylmethyl)-phosphinoylmethyl]-butyric acid
5za 4-Carbamoyl-2-(hydroxy-undecyl-phosphinoylmethyl)-butyric acid
5zb 4-Carbamoyl-2-(heptyl-hydroxy-phosphinoylmethyl)-butyric acid
5zc 4-Carbamoyl-2-[hydroxy-(4-isopropyl-cyclohexylmethyl)-phosphinoylmethyl]-butyric acid
5zd 4-Carbamoyl-2-[(6-ethyl-3-methyl-octyl)-hydroxy-phosphinoylmethyl]-butyric acid
5ze 4-Carbamoyl-2-[hydroxy-(3,7,11-trimethyl-dodecyl)-phosphinoylmethyl]-butyric acid
5zf 4-Carbamoyl-2-{[hydroxy-[2-methyl-4-(2,2,3-trimethyl-cyclopentyl)-butyl]-phosphinoylmethyl}-butyric acid
5zg 4-Carbamoyl-2-(hydroxyl-nonyl-phosphinoylmethyl)-butyric acid.

Structures of these compounds are set out below:

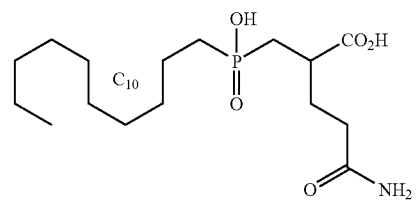

5a

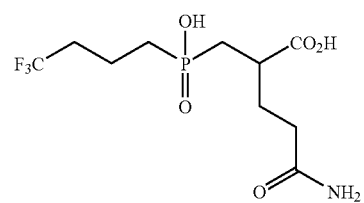

5b

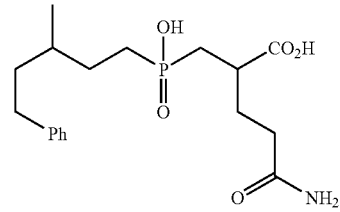

5c

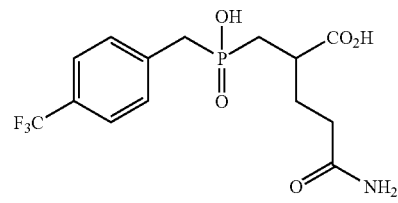

5d

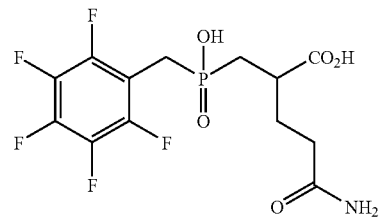

5e

-continued
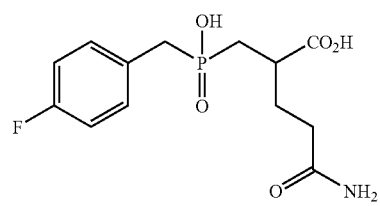
5f
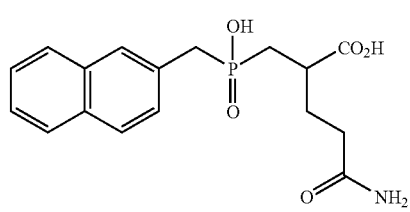
5g
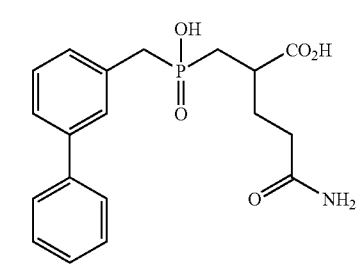
5h
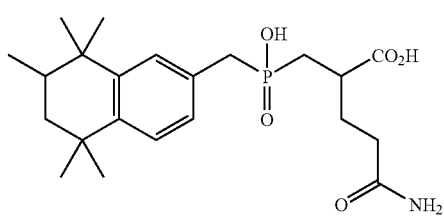
5i
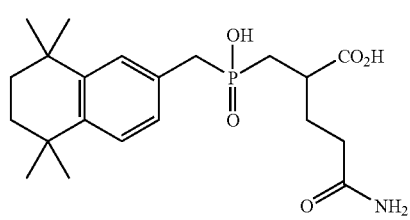
5k
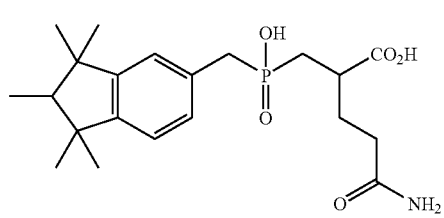
5l
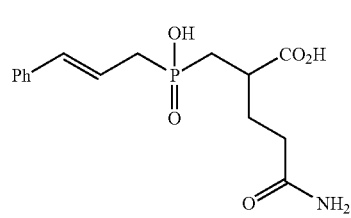
5m
-continued
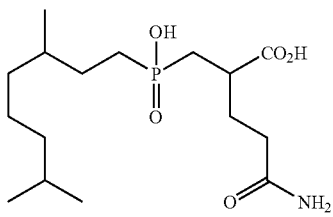
5n
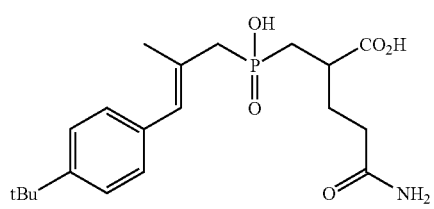
5o
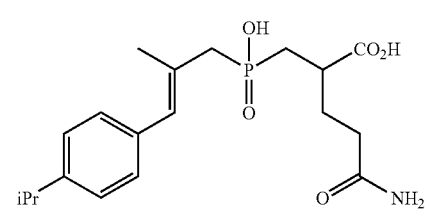
5p
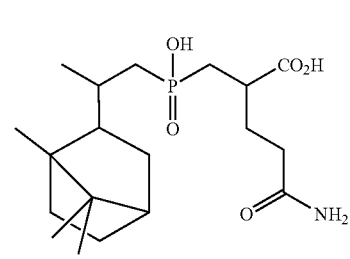
5q
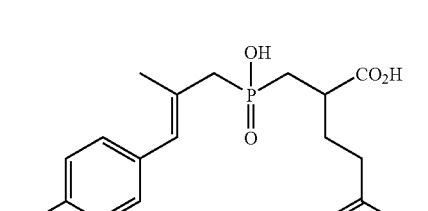
5r
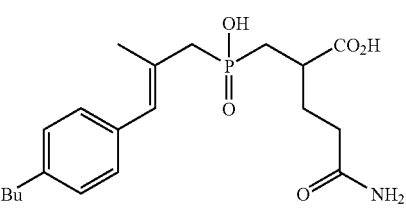
5s
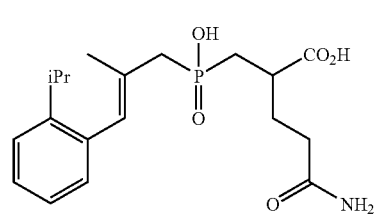
5t

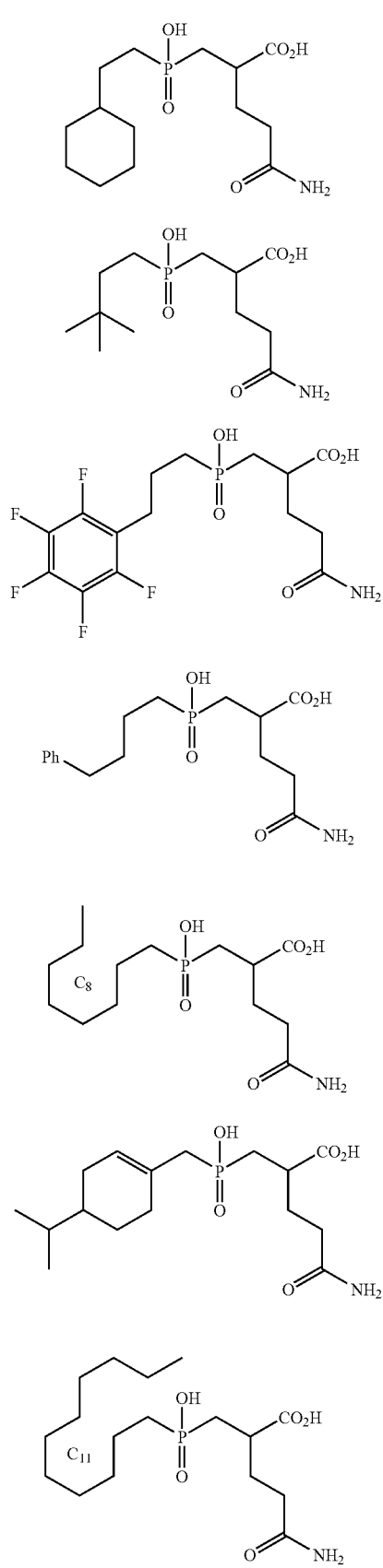
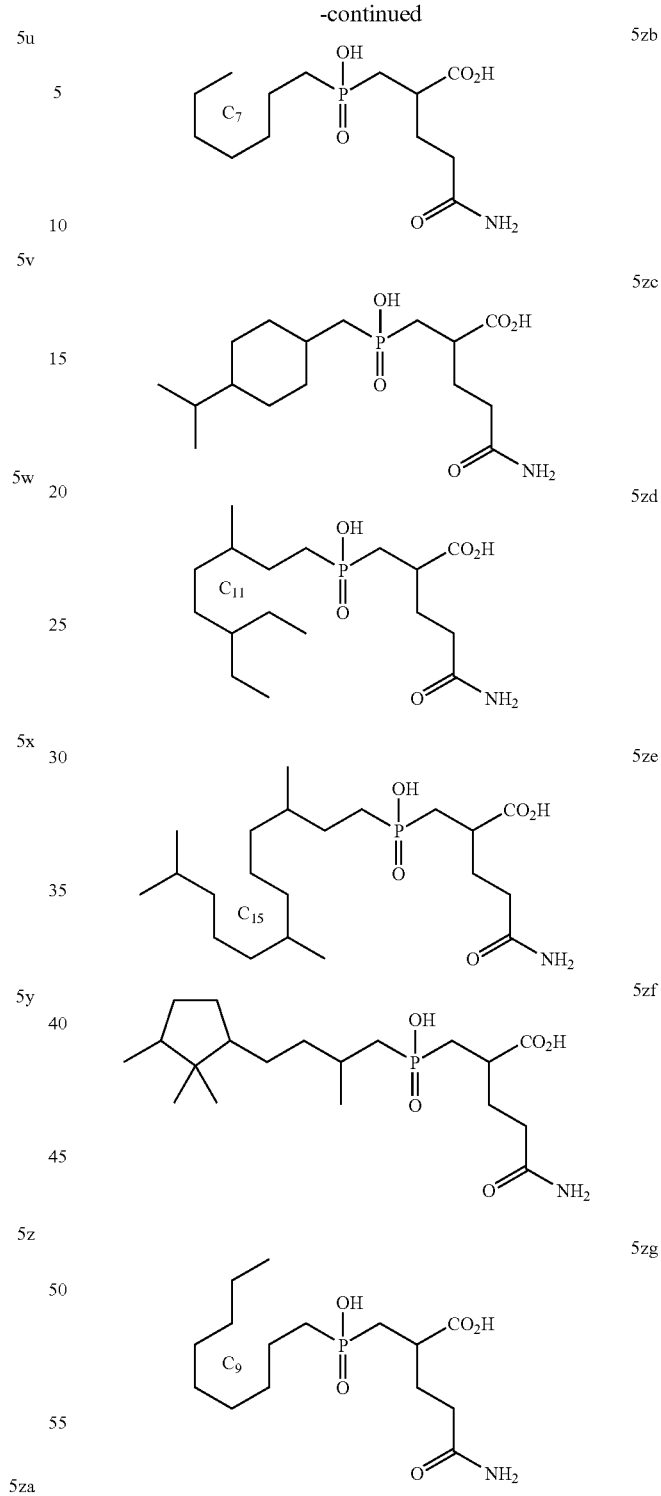
The following Examples are described with reference to Scheme 1 and Scheme 2. All compounds referred to in the Examples are defined by the combination of the corresponding compound number given in Scheme 1 or Scheme 2 and the letter code of the corresponding "R" residue. For example (4l) stands for compound 4 of Scheme 1, wherein R is 1,1,3,3-tetramethyl-indan-5-yl.

Example 1

A) Preparation of 2-Hydroxyphosphinoylmethyl-4-(trityl-carbamoyl)-butyric acid ethyl ester (2) (Step A of Scheme 1)

In a 500 mL flask equipped with a septum and a condenser, 25 g (0.3 mol) ammonium phosphinate and 49 g (0.3 mol) HMDS are heated under $N_2$ at 110° C. for 3.5 h. The reaction mixture is cooled to 5° C. where 25 g acrylate 1 in 150 ml dichloromethane is added. The mixture is stirred for 16 h at room temperature. Work-up: 1 N HCl and $CH_2Cl_2$ are added. The organic phase is washed with 1 N HCl, the combined acidic phases are re-extracted with $CH_2Cl_2$. The combined organic phases are dried over $MgSO_4$, evaporated under reduced pressure and dried at 50° C. under high vacuum yielding 28.8 g of phosphinic acid 2.

Yield: Quant; M.p.:152-154° C. (white solid); Purity: 89% ($^{31}$P-NMR) $^{31}$P-NMR (CDCl$_3$, 400 MHz): 32.0 ppm (s). MS (ESI neg.): 957 [2M–H], 478 [M–H]. $^1$H-NMR (CDCl$_3$, 400 MHz): 1.2 (t, 3H), 1.8 (m, 1H), 1.9 (2H), 2.05 (m, 1H), 2.25 (m, 1H), 2.7 (m, 1H), 4.1 (q, 2H), 6.3-7.7 (d, 1H, P—H, J=560 Hz), 6.9 (s, 1H, NH), 7.2 (15H, trityl-H), 8.2 (1H, P—OH). $^{13}$C-NMR (CDCl$_3$, 400 MHz): 14.2 (CH$_3$), 28.7 (d, CH$_2$), 30.8, 31.8 (d, P—CH$_2$), 34.3 (s, CH$_2$), 38.2 (CH), 61.2 (OCH$_2$), 70.5 (Ph$_3$C), 127.0 (3C, Trityl-CH), 127.9 (6C, Trityl-CH), 128.7 (6C, Trityl-CH), 144.6 (3C, Trityl-C), 171.0 (C=O), 174.0 (C=O).

B) Preparation of 2-[Hydroxy-(1,1,3,3-tetramethyl-indan-5-ylmethyl)-phosphinoyl-methyl]-4-(trityl-carbamoyl)-butyric acid ethyl ester (41) (Step B of Scheme 1)

In a 100 mL flask equipped with a septum and a condenser, monoalkylphosphinic acid 2 (3 g, 6.4 mmol) is dissolved in dry $CH_2Cl_2$ (20 ml). 5-Bromomethyl-1,1,3,3-tetra-methyl-indan 61(1.9 g, 7 mmol) and BSA (3.9 g, 19 mmol) are added and the mixture is stirred 72 h at 25° C. Work-up: The mixture is poured on 1N HCl. The organic phase is washed with 1N HCl, the combined acidic phases are re-extracted with 1N HCl. The combined organic phases are dried over $MgSO_4$, evaporated under reduced pressure and dried at 50° C. under high vacuum to give 4.77 g of the bisalkylated phosphinic acid 41.

Yield: Quant; Purity: 82% ($^{31}$P-NMR) $^{31}$P-NMR (CDCl$_3$, 400MHz): 53.8 ppm (s). MS (ESI neg.): 1329 (10% [2M–H]), 664 (100% [M–H]), 494 (30%). $^1$H-NMR (CDCl$_3$, 400MHz): 1.2 (t, 3H), 1.3 (14H), 1.7 (m, 1H), 1.9 (d, 2H, P—CH$_2$), 2.1 (m, 1H), 2.25 (2H), 2.7 (m, 1H), 3.0 (d, 2H, P—CH$_2$), 4.1 (q, 2H, OCH$_2$), 6.85 (s, 1H, NH), 7.2 (15H, trityl-H), 8.4 (s, 1H, P—OH).

Whereas this synthesis is described with reference to the "R" residue relating to compound 4l above, this synthesis is carried out for the preparation of other benzylic, or allylic phosphinoyl compounds whose "R" residues correspond to the compounds 4d, 4e, 4g, 4h, 4i, 4k, 4m, 4n, 4o, 4p, 4q, 4r, 4s, 4zd, 4ze and 4zf.

The 3 eq BSA of the above procedure can be replaced by 5-7 eq HMDS and the work-up can be simplified by addition of ethanol followed by concentration. In this way 4e, 4f and 4n were prepared.

C) Preparation of 4-Carbamoyl-2-[hydroxy-(4,4,4-trifluoro-butyl)-phosphinoylmethyl]-butyric acid (4b): (Step C of Scheme 1)

0.3 g (1.7 mmol) (4,4,4-trifluoro-butyl)-phosphinic acid 3b (0.3 g, 1.7 mmol) is dissolved in HMDS (1.4 g, 8.5 mmol) at room temperature and heated at 130° C. for 4 h. At 80° C. acrylate 1 (0.7 g, 1.7 mmol) is added and the reaction mixture heated at 130° C. for 16 h. Ethanol is added at 60° C. and the mixture refluxed for 30 min. The solvents are removed under reduced pressure and the residue is dried at 50° C. under high vacuum for 8 h to yield 0.9 g of 4b.

Yield: 89%; Purity: ~80% ($^1$H-NMR) $^{31}$P-NMR (CDCl$_3$, 400 MHz): 45.3 ppm (s). MS (ESI neg.): 670 (8% [M+NaOAc—H], 588 (100% [M–H]). $^1$H-NMR (CDCl$_3$, 400 MHz): 1.2 (t, 3H), 1.55 (m, 2H), 1.7 (m, 1H), 1.8 (3H), 1.95 (m, 1H), 2.15 (3H), 2.2 (m, 1H), 2.4 (m, 1H), 2.75 (m, 1H), 4.1 (q, 2H), 6.8 (s, 1H, NH), 7.2 (Trityl-H).

Whereas this synthesis is described with reference to the "R" residue relating to compound 4b (above), this synthesis is carried out for the preparation of other phosphinoyl compounds whose "R" residues correspond to the compounds 4a, 4c, 4f, 4i, 4t, 4u, 4v, 4w, 4x, 4y, 4z, 4za to 4zc and 4zg.

Example 2

Preparation of 4-Carbamoyl-2-[(3,7-dimethyl-octyl)-hydroxy-phosphinoyl-methyl]-butyric acid (5n) (Steps D,E,F of Scheme 1)

Step D: 288 g (0.4 mol) of the P-geranyl phosphinoyl compound 4n (prepared according to Example 1B) is dissolved in 1.4L ethanol at 70° C. 58 g of platinum (2.5% on charcoal/H$_2$O 1:1) is added at room temperature and the mixture is stirred under hydrogen for several days until complete hydrogenation (of the 2 double bonds) is detected by $^1$H-NMR or MS/ESI. The mixture is filtered over Celite which is washed with 0.3L ethanol.

Step E: 2L LiOH (1N in H$_2$O) are added to the filtrate. Under stirring the solution is heated to 50° C. for 1-2 days until complete hydrolysis is detected by H-NMR or MS/ESI. The solution is neutralized by addition of ca. 250 ml conc. HCl. The supernatant solution is decanted from the precipitates, the ethanol is removed from this solution under reduced pressure and the remaining H$_2$O phase is extracted with 3×0.5L CH$_2$Cl$_2$. The above precipitates are dissolved in 1.5L CH$_2$Cl$_2$. The combined organic layers are dried over MgSO$_4$, filtered and concentrated under reduced pressure to give 206 g of a reddish solid.

Step F: The resulting material of Step E (ca. 0.35 mol) is dissolved in 2.5L trifluoroacetic acid. 120 g (0.75 mol) triisopropylsilane is added and the resulting suspension stirred for 4 h at room temperature. The trifluoroacetic acid is removed under reduced pressure. 3L H$_2$O is added to the residue und the resulting suspension stirred at 60° C. for 15 min. The supernatant water-phase is decanted off. 3L NH$_3$ (6% in water) is added to the residue, the resulting suspension is stirred at 60° C. for 15 min and filtered over Celite. The filtrate is divided into 3 portions and filtered over 3 Chromabond C18-columns filled each with 10 g RP (Reverse Phase) material. The filtrates are concentrated under reduced pressure. To the residues toluene is added and removed under reduced pressure (3 times). Drying under high vacuum gives 109 g of a white-yellow solid foam.

Yield: 78% (based on substrate 4n); Purity: 90% ($^{31}$P-NMR) $^{31}$P-NMR (D$_2$O, 400 MHz): 44.8 ppm (s). MS (ESI neg.): 348 (100% [M–H]). $^1$H-NMR (D$_2$O, 400 MHz): 1.2

(2d, 9H), 1.0-1.7 (13H), 1.8-2.0 (3H), 2.2-2.3 (t, 2H, P—CH$_2$), 2.5-2.6 (1H), 4.8 (4H, CO$_2$H, POH, NH$_2$) ppm. $^{13}$C-NMR (D$_2$O, 400 MHz): 18.7, 18.8, 22.4, 22.5, 24.6 (CH$_2$), 27.7, 27.2 and 28 (d, P—CH$_2$), 29.3 (CH$_2$), 30.7 and 31.7 (d, P—CH$_2$), 32.8 (CH$_2$), 33.7, 33.8, 36.5 (CH$_2$) 40.0, 178.2 (C=O), 179.6 (C=O).

Whereas this synthesis is described with reference to the "R" residue relating to compound 5n (above), this synthesis is carried out for the preparation of other phosphinoyl compounds whose "R" residues correspond to the compounds 5zc, 5zd, 5ze and 5zf which are derived from P-alkyl-, and P-γ,γ-disubstituted allyl-phosphinoyl compounds 4zc, 4zd, 4ze, and 4zf which are prone to oxaphospholane formation under acidic conditions. Therefore the corresponding C=C-double bonds were removed by hydrogenation, prior to hydrolysis/detritylation.

All other phosphinoyl compounds (5a-5m, 5o to 5zb and 5zg) were prepared without prior hydrogenation (Step D) just by hydrolysis/detritylation (Steps E and F).

Compound 5zc was also prepared following the general procedure of Example 2 except that the hydrogenation was carried out over Raney-Nickel in place of platinum on charcoal (Step D).

Example 3

Preparation of 7-Bromomethyl-1,2,4,4-pentamethyl-1,2,3,4-tetrahydro-naphthalene 6i: (Step G of Scheme 2)

In a 100 mL flask equipped with thermometer, septum and a condenser 21.6 g (0.1 mol) 1,1,2,4,4,7-hexamethyl-1,2,3,4-tetrahydro-naphthalene (prepared as described by Wood, T. F.; Easter, W. M., Jr.; Carpenter, M. S.; Angiolini, J. Org. Chem. 28, 2248 (1963)) is heated to 170° C. 16 g (0.1 mol) Bromine is added and the reaction mixture stirred for 5 h at 170° C. The content of the flask is fractionated over a Vigreux column (110° C., 4 mbar) giving 17 g (58%) 6i as a colorless liquid.

Yield: 58%; GC-purity: 71% GC/MS: 294/296 (5%, [M]$^+$), 279/281 (10%, [M-CH$_3$]$^+$), 215 (100%, [M-Br]$^+$, 201 (65%, [M-CH$_2$Br]$^+$), 157 (55%). $^1$H-NMR (CDCl$_3$, 400 MHz): 0.95 (d, 3H), 1.05 (s, 3H), 1.25 (s, 3H), 1.3 (s, 3H), 1.35 (s, 3H), 1.4 (dd, 1H, A), 1.65 (dd, 1H, B), 1.85 (m, 1H, CH), 4.5 (s, 2H, CH$_2$Br), 7.15 (d, 1H, Ar—H), 7.25 (d, 1H, Ar—H), 7.35 (s, 1H, Ar—H). $^{13}$C-NMR (CDCl$_3$, 400 MHz): 16.8 (CH$_3$), 25.0 (CH$_3$), 28.5 (CH$_3$), 31.9 (CH$_3$), 32.3 (CH$_3$), 34.3 (CH$_2$), 34.4 (C), 34.5 (CH), 37.8 (C), 43.5 (CH$_2$Br), 126.2, 127.0, 127.7 (Ar—CH), 134.7, 145.2, 146.5 (Ar—C).

Example 4

Preparation of (5-Iodo-3-methyl-pentyl)-benzene 7c: (Step H of Scheme 2)

5 g (28 mmol) Phenoxanol (3-Methyl-5-phenyl-pentan-1-ol) is dissolved in 200 ml dichloromethane under nitrogen and stirring. Triphenylphosphine (8.8 g, 34 mmol) and 4.2 g (53 mmol) pyridine are added at 25° C. After cooling to 0° C. iodine (8.5 g, 34 mmol) is added. After 2 h stirring at 0° C. the reaction mixture is poured on ice-cooled 1 N HCl and extracted with dichloromethane. The combined organic phases are washed with 10% Na$_2$S$_2$O$_3$, sat. NaHCO$_3$ and sat. NaCl. Drying over MgSO$_4$ and evaporation gives 17 g of a residue which is triturated with hexane and filtered over a 5 cm Silicagel pad. The filtrate is evaporated under reduced pressure and dried under high vacuum giving 7.1 g of 7c as a colorless oil.

Yield: 88%; Purity: >95% (GC, NMR) GC/MS: 288 (5%, [M]$^+$), 161 (10%, [M-I]$^+$), 119 (5%), 105 (20%, [PhCH$_2$CH$_2$]$^+$), 91 (100%, [[PhCH$_2$]$^+$). $^1$H-NMR (CDCl$_3$, 400 MHz): 0.95 (d, 3H, CH$_3$), 1.45 (m, 1H), 1.6 (3H), 1.9 (m, 1H), 2.6 (2H, PhCH$_2$), 3.2 (2H, CH$_2$I), 7.2 (5H, ArH). $^{13}$C-NMR (CDCl$_3$, 400 MHz): 4.9 (CH$_2$), 18.7 (CH$_3$), 33.3 (CH$_2$), 33.7 (CH$_3$), 38.2 (CH$_2$), 40.9 (CH$_2$), 125.8, 128.3, 128.4 (ArCH), 142.5 (ArC).

Example 4

Preparation of E-1-(3-Bromo-2-methyl-propenyl)-4-tert-butyl-benzene 8o: (Steps I and J of Scheme 2)

20 g (0.1 mol) E-3-(4-tert-Butyl-phenyl)-2-methyl-propenal (prepared according to U.S. Pat. No. 4,435,585) is added to a stirred solution of 1.2 g (32 mmol) of sodium borohydride in 20 ml of methanol at 0° C. After 2 h at room temperature quantitative conversion is checked by TLC. The reaction mixture is poured onto 40 ml saturated sodium chloride and extracted with tert-butyl methyl ether. Drying over magnesium sulfate and evaporation of the solvent gives the crude allylic alcohol (19.2 g, 94%), which is transferred to the following bromination reaction without further purification.

5 g (24 mmol) of the crude allylic alcohol is dissolved in 35 ml of dry diethyl ether under nitrogen. At 0° C. phosphorus tribromide (0.95 ml, 10 mmol) is added via syringe. The reaction is stirred at 0° C. for 4 h, poured onto ice and extracted three times with diethyl ether. The organic layer is washed with saturated NaHCO$_3$ and dried over MgSO$_4$. The solvent is removed under reduced pressure giving the crude allylic bromide 5.7 g of 8o.

Yield: 5.7 g (87% from the aldehyde); Purity: >95% (GC, NMR) GC/MS: 266/268 (3%, [M]$^+$), 251 (1%, [M-CH$_3$]$^+$), 188 (25%, [M-Br]$^+$), 173 (55%, [M-Br—CH$_3$]$^+$), 157(10%), 131 (55%), 115(22%), 91 (16%), 57(100%). $^1$H-NMR (CDCl$_3$, 400 MHz): 1.3 (s, 9H, tBu-CH$_3$), 2.0 (s, 3H, CH$_3$), 4.15 (s, 2H, CH$_2$Br), 6.6 (s, 1H, =CH), 7.22 (d, 2H, Ar—H), 7.35 (s, 2H, Ar—H). $^{13}$C-NMR (CDCl$_3$, 400 MHz): 16.6 (CH$_3$), 31.3 (3C, tBu-CH$_3$), 34.6 (tBu-C), 42.6 (CH$_2$), 125.2, 128.7 (ArCH), 130.0 (=CH), 133.7, 134.0 (Ar—C), 150.2 (=C)

Example 6

Preparation of (3,7-Dimethyl-octa-2,6-dienyl)-phosphinic acid 3n: (Step K of Scheme 2)

In a 750 mL flask equipped with septum, thermometer and condenser, ammonium phosphinate (25 g, 0.3 mol) and HMDS (51 g, 0.32 mmol) are heated under N$_2$ at 110° C. for 3 h. The reaction mixture is cooled to 0° C. 300 mL dried CH$_2$Cl$_2$ are added followed by the addition of geranyl bromide (13.1 g, 60 mmol). The mixture is stirred for 16 h at room temperature. 10 ml methanol are added and the fine suspension is filtered over a double filter layer. The filtrate is concentrated under reduced pressure. 10% Na$_2$CO$_3$ and tert-butyl methyl ether are added, the phases are separated and the alkaline layer purified with tert-butyl methyl ether. The alkaline layer is treated with conc. HCl until pH=1 and is then 3 times extracted with dichloromethane. Drying of the dichloromethane layer over MgSO$_4$ and evaporation give 13.7 g (81%) of 3n as orange oil.

Yield: 13.7 g (81%); Purity: 77% ($^{31}$P-NMR) $^{31}$P-NMR (CDCl$_3$, 400 MHz): 34.9 ppm (s). MS (ESI neg.): 403 (10% [2M-H]$^+$), 201 (100%, [M-H]$^+$). $^1$H-NMR (CDCl$_3$, 400

MHz): 1.2 (d, 1H), 1.6 (s, 3H, CH$_3$), 1.6 (6H, 2 CH$_3$), 2.1 (4H, CH$_2$CH$_2$), 2.6 (dd, 2H, P—CH$_2$), 5.1 (1H, =CH), 5.15 (1H, =CH), 6.22 and 7.6 (d, 1H, J=548 Hz, P—H), 11.8 (s, 1H, POH). $^{13}$C-NMR (CDCl$_3$, 400 MHz): 16.5 (CH$_3$), 17.6 (CH$_3$), 25.6 (CH$_3$), 26.4 (CH$_2$), 30.4 and 29.5 (d, P—CH$_2$), 39.7 (CH$_2$), 110.5 (=CH), 123.7 (=CH), 131.7 (=C), 141.9 (=C).

Example 7

Preparation of (3-phenyl-propyl)-phosphinic acid 3t: (Step L of Scheme 2)

To a solution of NaH$_2$PO$_2$(H$_2$O) (13.2 g, 0.125 mol) and allylbenzene (6.6 g, 56 mmol) in methanol (250 ml) is added triethylborane (1M in THF, 50 ml, 50 mmol) at room temperature in an open 500 ml flask. The solution is stirred for 2 h at room temperature. The reaction mixture is concentrated under reduced pressure. 100 ml saturated KHSO$_4$ are added to the residue followed by extraction (200, 100 and 70 ml) with ethyl acetate. To the combined ethyl acetate layers are added 40 ml 10% Na$_2$CO$_3$. Under vigorous stirring and dropwise addition of conc. NaOH the biphasic mixture is adjusted to pH=10. The organic phase is separated and the alkaline phase adjusted to pH=2 by addition of conc. HCl. Extraction with chloroform (3×100 ml), drying of the combined organic layer over MgSO$_4$ and evaporation gives 5.4 g of crude 3t (61%).

Yield: 61%; Purity: 84% ($^{31}$P-NMR) $^{31}$P-NMR (CDCl$_3$, 400 MHz): 38.2 ppm (s). MS (ESI neg.): 265 (6% [M–H+ NaOAc]$^+$), 183 (100%, [M–H]$^+$). $^1$H-NMR (CDCl$_3$, 400 MHz): 1.75 (m, 2H, CH$_2$), 1.9 (m, 2H, CH$_2$), 2.76 (t, 2H, PhCH$_2$), 6.4 and 7.7 (d, 1H, J=548 Hz, P—H), 11.4 (s, 1H, POH).

Example 8

Measuring Inhibitory Activity

Cellular Extracts of *Corynebacterium striatum* Ax 20 (DSM 14267) are prepared by mechanical disruption and subsequent centrifugation.

The extract (50 µl ml corresponding to 0.2 ml initial cell culture) is added to 50 µl of Buffer A (Phosphate Buffer, pH 7). Various concentrations of the compounds of the present invention are added in a volume of 40 µl, and after 10 min preincubation at 37° C., the reaction is and amended with 10 µl of substrate (Nα-lauroyl-L-glutamine, final concentration 50 µM). The samples are incubated for 15 min and then the reaction is stopped by adding 75 µl of Fluorescamine (2.5 mM dissolved in Acetonitrile). The fluorescence resulting from derivatization of the released glutamine with fluorescamine is determined at an excitation wavelength of 381 nm and an emission wavelength of 470 nm.

By comparing the samples containing compounds of the present invention with control samples with enzyme and substrate only, the inhibition (%) is calculated. Alternatively, the same assay is made with a recombinantly formed enzyme produced with a strain containing an expression vector comprising a nucleic acid sequence encoding for the enzyme. The results for some compounds of the present invention are listed in Table 1.

TABLE 1

| Enzyme inhibition | | | |
|---|---|---|---|
| Compound | IC$_{50}$ value (nM) | Compound | IC$_{50}$ value (nM) |
| 5a | 30.3 | 5x | 40 |
| 5c | 11.5 | 5z | 32 |
| 5g | 137.5 | 5y | 17.9 |
| 5t | 125 | 5n | 9 |

In order to evaluate enzyme activity in intact cells, stationary phase living cells of Ax20 are harvested and resuspended in Buffer A to an optical density at 600 nm of 0.25. Inhibitory compounds are added at various concentrations, and after a preincubation of 15 min, the substrate (Nα-lauroyl-L-glutamine, 1 mM final concentration) is added. The samples are incubated for 1 h and then extracted with MTBE and HCl and analysed for released lauric acid using capillary GC. By comparing the samples containing compounds of the present invention with control samples with bacteria and substrate only, the inhibition (%) is calculated. By comparing the inhibitory capacity of the compounds on the isolated enzyme with the values obtained using intact cells, the relative uptake of the compounds by the cells can be assessed. From Table 2 it appears, that compounds of the present invention can cross the bacterial cell wall and cytoplasmatic membrane, and thus can have inhibitory activity in living cells.

TABLE 2

Inhibition of the enzymatic activity in living cells at the concentration of 0.2 micromolar

| Compound | % inhibition of release of fatty acids by *Corynebacterium* Ax20 at a concentration of 0.2 µM |
|---|---|
| 5a | 60.9 |
| 5c | 70.5 |
| 5n | 69.5 |
| 5y | 64.9 |

The invention claimed is:

1. A compound according to the following formula (I)

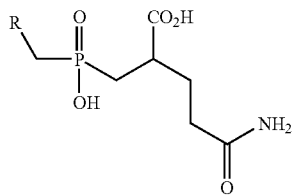

wherein R is a substituted alkyl, benzyl or allyl residue selected from the group consisting of nonyl; 333-trifluoro-propyl; 2-methyl-4-phenyl-butyl; 4-trifluoromethyl-phenyl; pentafluorophenyl; 4-fluoro-phenyl; naphthalene-2-yl; biphenyl-2-yl; 5,5,7,8,8-pentamethyl-5,6,7,8-tetrahydro-naphthalene-2-yl; 5,5,8,8-tetramethyl-5,6,7,8-tetrahydro-naphthalen-2-yl; 1,1,3,3-tetramethyl-indan-5-yl; styryl; 2,6-dimethyl-heptyl; 2-(4-tert-Butyl-phenyl)-1-methyl-vinyl; 2-(4-isopropyl-phenyl)-1-methyl-vinyl; 1-(1,7,7-Trimethyl-bicyclo[2.2.1]hept-2-yl)-ethyl; 2-(4-isobutyl-phenyl)-1-methyl-vinyl; 2-(2-isopropyl-phenyl)-1-methyl-ethenyl; 2-phenyl-ethyl; cyclohexyl-methyl; 2,2-dimethyl-propyl; 2-(pentafluorophenyl)-ethyl; 3-phenyl-propyl; heptyl; 4-isopropyl-cyclohex-1-enyl; decyl; hexyl; trans-4-isopropyl-cyclohexyl; 5-ethyl-2-methyl-heptyl; 2,6,10-trimethyl-undecyl; 1-methyl-3-(2,2,3-trimethyl-cyclopentyl)-propyl; and octyl.

2. A composition comprising a compound claimed in claim 1.

3. A composition according to claim 2 wherein the compound is present in amounts of about 0.01 to 0.5% by weight.

4. A composition according to claim 2 selected from cosmetic and personal care products, in particular deo-sticks, roll-ons, pump-sprays, aerosols, deodorant soaps, powders, solutions, gels, creams, sticks, balms and lotions.

5. A method of suppressing axillary malodour comprising the step of providing a composition for application to the skin of a person in need of treatment, said composition containing an inhibitor compound and a dermatologicatly acceptable vehicle therefore, said compound being selected from one or more compounds as defined by claim 1.

* * * * *